(12) United States Patent
Walsh et al.

(10) Patent No.: US 11,272,939 B2
(45) Date of Patent: Mar. 15, 2022

(54) INTRASACCULAR FLOW DIVERTER FOR TREATING CEREBRAL ANEURYSMS

(71) Applicant: DePuy Synthes Products, Inc., Raynham, MA (US)

(72) Inventors: Michael Walsh, Foster City, CA (US); Chad Roue, Raynham, MA (US); Marc Jensen, Los Gatos, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 392 days.

(21) Appl. No.: 16/224,223

(22) Filed: Dec. 18, 2018

(65) Prior Publication Data

US 2020/0187952 A1 Jun. 18, 2020

(51) Int. Cl.
*A61B 17/12* (2006.01)

(52) U.S. Cl.
CPC .... *A61B 17/12113* (2013.01); *A61B 17/1214* (2013.01); *A61B 17/12031* (2013.01); *A61B 2017/1205* (2013.01)

(58) Field of Classification Search
None
See application file for complete search history.

(56) References Cited

U.S. PATENT DOCUMENTS

| | | | |
|---|---|---|---|
| 2,849,002 A | 8/1958 | Oddo | |
| 3,480,017 A | 11/1969 | Shute | |
| 4,085,757 A | 4/1978 | Pevsner | |
| 4,282,875 A | 4/1981 | Serbinenko et al. | |
| 4,364,392 A | 12/1982 | Strother et al. | |
| 4,395,806 A | 8/1983 | Wonder et al. | |
| 4,517,979 A | 5/1985 | Pecenka | |
| 4,545,367 A | 10/1985 | Tucci | |
| 4,836,204 A | 6/1989 | Landymore et al. | |

(Continued)

FOREIGN PATENT DOCUMENTS

| | | |
|---|---|---|
| CA | 2395796 A1 | 7/2001 |
| CA | 2598048 A1 | 5/2008 |

(Continued)

OTHER PUBLICATIONS

Altes et al. Creation of Saccular Aneurysms in the Rabbit: A Model Suitable for Testing Endovascular Devices. AJR 2000; 174: 349-354.

(Continued)

*Primary Examiner* — Shaun L David
(74) *Attorney, Agent, or Firm* — Troutman Pepper Hamilton Sanders LLP

(57) ABSTRACT

Implants can be used as flow diverters for treating aneurysms. Implants can include a stabilizing frame for anchoring the implant and an occluding element for diverting blood flow from the aneurysm neck. The stabilizing frame can have two parts, the first part sized to anchor within the sac of the aneurysm and the exterior part sized to anchor against a region of the blood vessel wall adjacent the aneurysm neck. The occluding element can be attached to the interior frame and positioned to occlude the aneurysm neck. The implant can have a central node that can be positioned near the center of the aneurysm neck at which the interior frame is attached to the exterior frame and from which the interior frame and the exterior frame extend.

18 Claims, 9 Drawing Sheets

(56) References Cited

U.S. PATENT DOCUMENTS

| | | |
|---|---|---|
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,916,235 A | 6/1999 | Guglielmi |
| 5,891,128 A | 7/1999 | Chin et al. |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 * | 1/2001 | Mazzocchi ........ A61B 17/0057 606/200 |
| 6,193,708 B1 * | 2/2001 | Ken ................ A61B 17/12022 606/1 |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford et al. |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones et al. |
| 6,454,780 B1 | 9/2002 | Wallace |
| 6,463,317 B1 | 10/2002 | Kucharczyk et al. |
| 6,506,204 B2 | 1/2003 | Mazzocchi et al. |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran et al. |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes |
| 9,161,758 B2 | 10/2015 | Figulla et al. |
| 9,232,992 B2 | 1/2016 | Heidner |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |

(56) References Cited

U.S. PATENT DOCUMENTS

| | | |
|---|---|---|
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Heisei et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Peterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisei et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1* | 10/2003 | Wallace ............ A61B 17/12172 606/200 |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney et al. |
| 2007/0088387 A1* | 4/2007 | Eskridge ............ A61B 17/12172 606/213 |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1* | 8/2007 | Eskridge ............ A61B 17/12022 606/213 |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka |
| 2009/0036877 A1 | 2/2009 | Nardone et al. |
| 2009/0062841 A1 | 3/2009 | Amplatz et al. |
| 2009/0099647 A1 | 4/2009 | Glimsdale et al. |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu et al. |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1* | 10/2013 | Cox .................... A61F 2/91 623/1.15 |
| 2013/0345738 A1* | 12/2013 | Eskridge .......... A61B 17/12113 606/198 |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2014/0358178 A1 | 12/2014 | Hewitt et al. |

(56) References Cited

U.S. PATENT DOCUMENTS

| | | |
|---|---|---|
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero |
| 2017/0079680 A1 | 3/2017 | Bowman |
| 2017/0079717 A1 | 3/2017 | Walsh et al. |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0114350 A1 | 8/2017 | Shimizu et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340333 A1* | 11/2017 | Badruddin ............... A61F 2/86 |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0069313 A1 | 3/2020 | Xu et al. |
| 2020/0268365 A1 | 8/2020 | Hebert et al. |

FOREIGN PATENT DOCUMENTS

| | | |
|---|---|---|
| CA | 2 431 594 A1 | 9/2009 |
| CN | 204 683 687 U | 10/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 1 003 422 A1 | 2/1999 |
| EP | 902704 B1 | 3/1999 |
| EP | 1 039 846 A1 | 6/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |

(56) References Cited

FOREIGN PATENT DOCUMENTS

| | | | |
|---|---|---|---|
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | 2015160721 A1 | 10/2015 |
| WO | 2015171268 A2 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | 2016/137997 A1 | 9/2016 |
| WO | WO 2017/161283 A1 | 9/2017 |
| WO | 2018/051187 A1 | 3/2018 |
| WO | WO 2012/034135 A1 | 3/2021 |

OTHER PUBLICATIONS

Schaffer, Advanced Materials & Processes, Oct. 2002, pp. 51-54.
Extended European Search Report issued in corresponding European Patent Application No. 19 21 7054 dated Mar. 17, 2020.
Extended European Search Report issued in corresponding European Patent Application No. 19 21 5277 dated May 12, 2020.
Extended European Search Report dated May 2, 2019 in corresponding European Application No. 18214052.5.

* cited by examiner

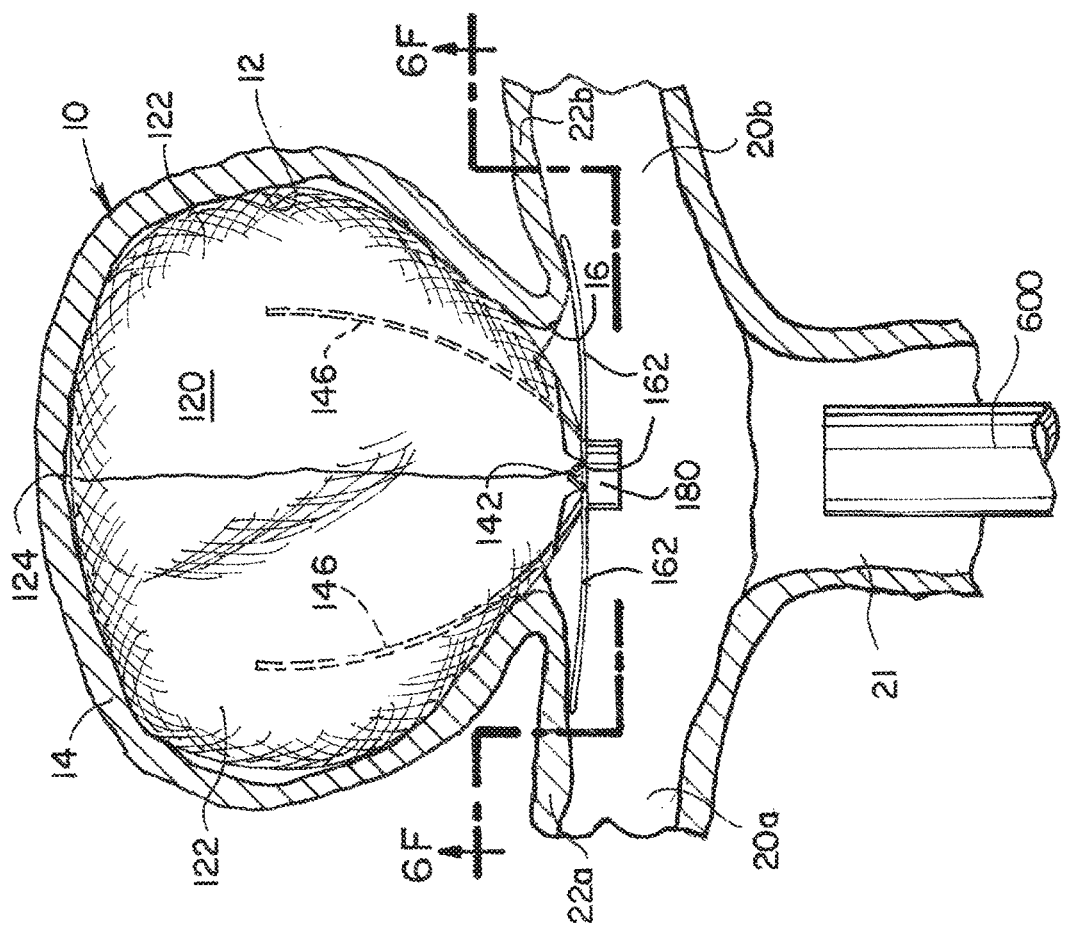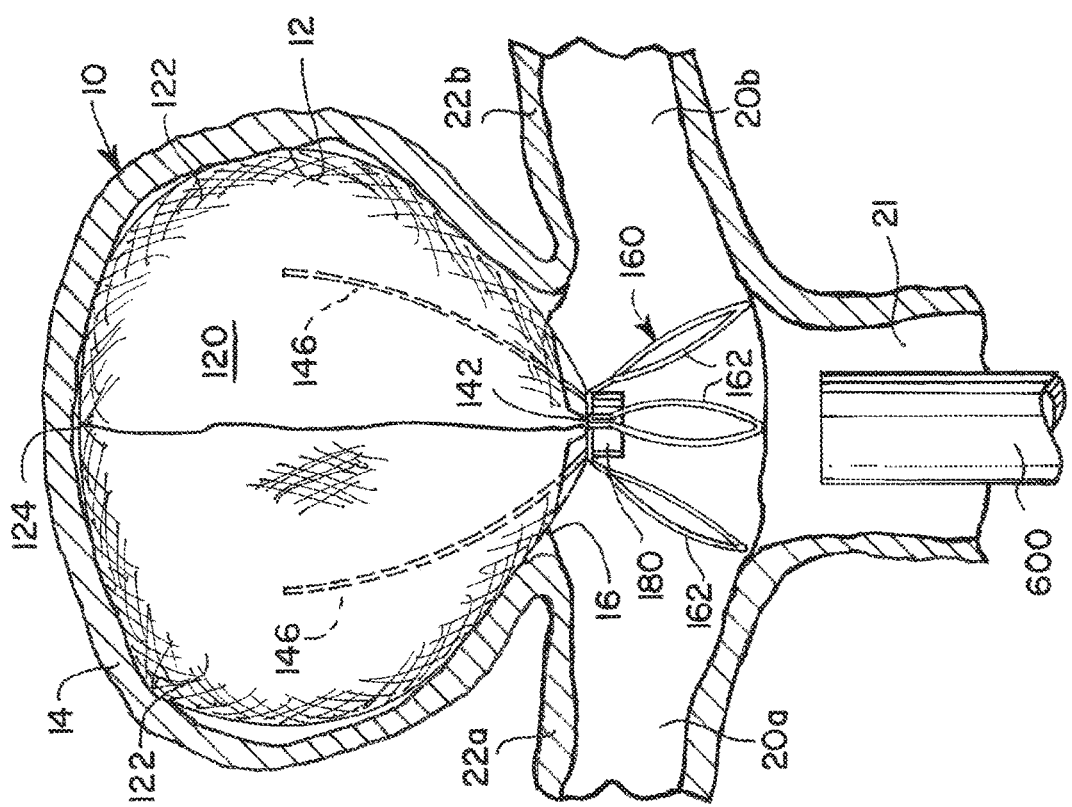

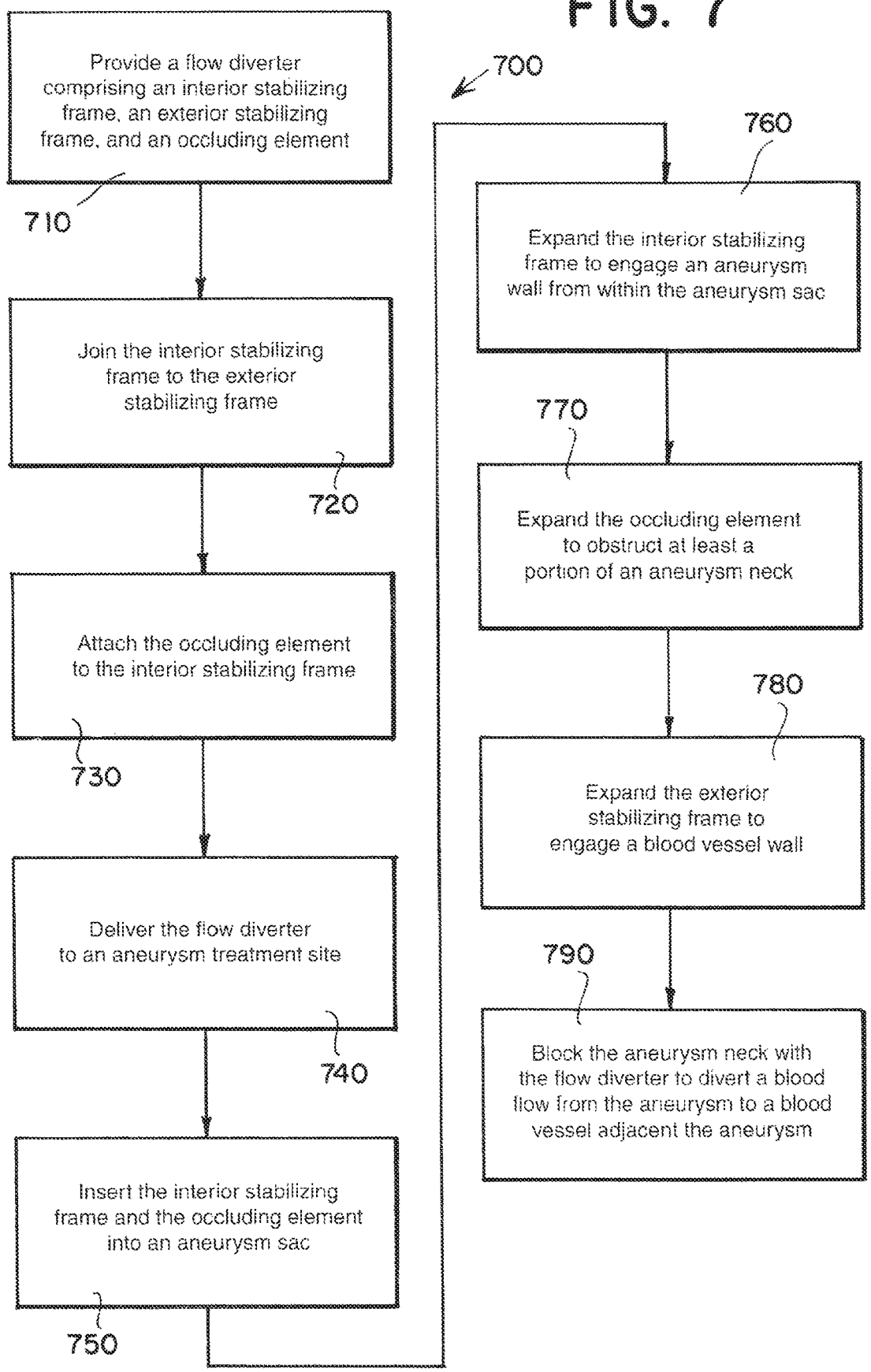

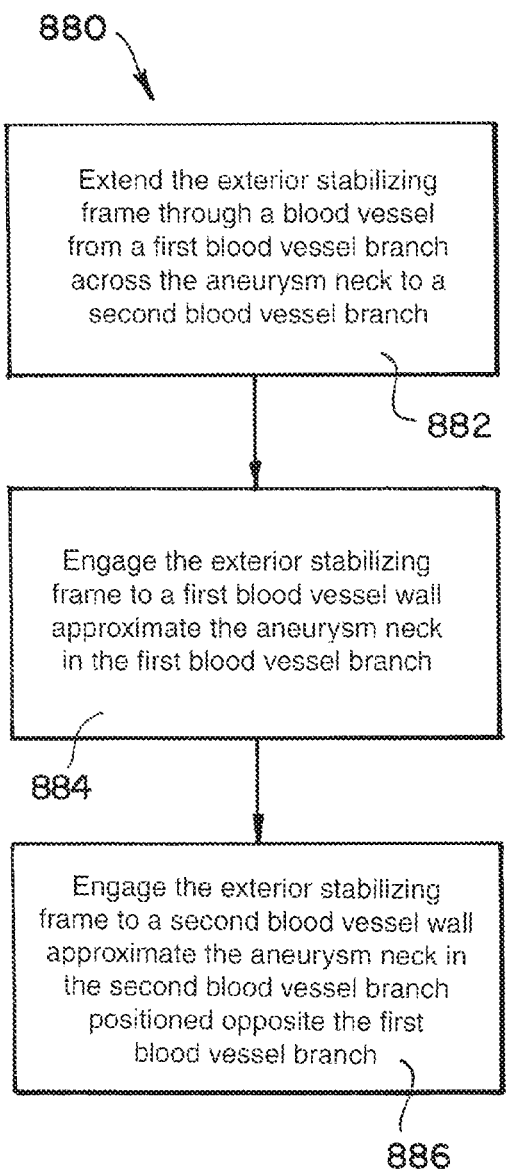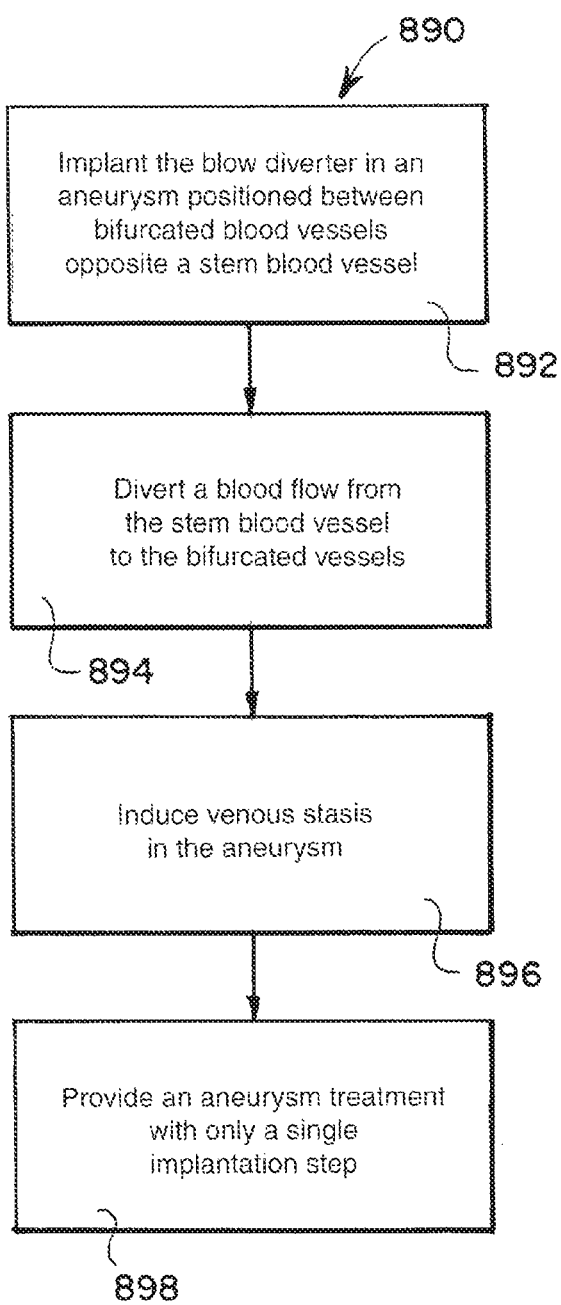

INTRASACCULAR FLOW DIVERTER FOR TREATING CEREBRAL ANEURYSMS

FIELD OF INVENTION

The present invention generally relates to aneurysm treatment devices, and more particularly, to flow diverters.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include implanting devices that fill the sac of the aneurysm with embolic material, divert blood from the aneurysm neck, or both to prevent blood flow into the aneurysm. When filling the aneurysm sac, the embolic material clots the blood, creating a thrombotic mass within the aneurysm. When treating the aneurysm neck, blood flow into the entrance of the aneurysm is inhibited and diverted to flow through a blood vessel, thereby inducing venous stasis in the aneurysm and facilitating a natural formation of a thrombotic mass within the aneurysm.

Current treatments primarily include implanting a stent and/or embolic coils. A stent can be expanded within a blood vessel to extend across the neck of the aneurysm, thereby effectively diverting blood flow away from the aneurysm and through the blood vessel; however, stents are typically not viable treatment devices for aneurysms located at a bifurcation because a stent can inhibit blood flow through the vasculature at the bifurcation. Embolic coils are typically used in current treatments for packing aneurysms, and in some instances, for treating the aneurysm neck; however, embolic coils are typically not viable treatment devices for wide neck aneurysms because the embolic coils can recanalize, provide poor coverage across the aneurysm neck, and/or extend into the adjoining blood vessel. Stents can be used in conjunction with embolic coils, and in such strategies, typically the embolic coils pack the aneurysm sac and the stent inhibits the coils from exiting the aneurysm. However, neither stents nor embolic coils are ideal treatment devices for wide neck aneurysms located at bifurcations.

A number of implant structures have been investigated for treating aneurysms located at bifurcations (such as disclosed in U.S. Pat. No. 10,004,510); however, there is an ongoing need for improved or alternative implant structures for treating aneurysms, particularly for treating wide neck aneurysms located at bifurcations.

SUMMARY

Embodiments presented herein include devices and implants for treating an aneurysm and methods for manufacturing and/or using the same. Implants can be used as flow diverters and can generally include a stabilizing frame for anchoring the implant and an occluding element for diverting blood flow from the aneurysm neck. The stabilizing frame can have an interior frame for anchoring within the sac of the aneurysm and an exterior frame for anchoring against a region of the blood vessel wall adjacent the aneurysm neck. The occluding element can be attached to the interior frame and positioned to occlude the aneurysm neck. The implant can have a central node at which the interior frame and exterior frame are connected and from which the interior frame and the exterior frame extend. When the implant is implanted, the central node can be positioned near a center of the aneurysm neck, the exterior frame can extend across the aneurysm neck outside of the aneurysm sac and the interior frame and the occluding element can extend across the aneurysm neck within the aneurysm sac.

An example device can include a central node, an interior stabilizing frame, an exterior stabilizing frame affixed to the interior stabilizing frame at the central node, and an occluding element affixed to the interior stabilizing frame. When the device is implanted, the central node can be positioned centrally within the opening of the aneurysm neck, the interior stabilizing frame can extend radially from the central node and distally into the sac of the aneurysm to engage the aneurysm wall, the exterior frame can extend radially from the central node and engage a first blood vessel wall in a first blood vessel branch and a second blood vessel wall in a second blood vessel branch, and the occluding element can be at least partially disposed in the aneurysm sac, extend across all or part of the aneurysm neck, and obstruct some or all of the aneurysm neck.

The combination of the interior stabilizing frame and the exterior stabilizing frame can be sufficient to maintain position of the implanted device. The sole combination of the interior stabilizing frame and the exterior stabilizing frame can affix the device to an aneurysm treatment site.

The occluding element can self-expand and conform to the interior wall of the aneurysm. The occluding element can partially or completely obstruct the aneurysm neck. The occluding element can at least partially fill the aneurysm sac.

The exterior stabilizing frame can have two stabilizing arms that each extend from the central node so that the stabilizing arms engage portions of blood vessel wall near the aneurysm neck. When the aneurysm is positioned at a bifurcation, the stabilizing arms can extend opposite each other and contact walls of two branch blood vessels.

The interior stabilizing frame can have at least three elongated members each having a first end positioned near the central node, a first segment extending from the first end across the aneurysm neck, and a second segment extending distally and conforming to the aneurysm wall.

The occluding element can have multiple oblong leaf structures that each extend from the aneurysm neck radially and distally such that each leaf at least partially occludes the aneurysm neck and at least partially conforms to the aneurysm wall. The oblong leaf structures can converge at a distal end of the device, and when implanted, the distal end of the device can be positioned near a distal surface of the aneurysm wall.

In another example, a blood flow diverter for treating an aneurysm can include a distally extending frame portion, an expandable shell joined to the distally extending frame portion, and a radially extending frame portion attached to the distally extending frame portion. When the blood flow diverter is implanted, the distally extending frame portion can be positioned within an aneurysm sac and provide a force against an aneurysm wall from within the aneurysm sac, the expandable shell can extend across at least a portion of an aneurysm neck and conform to the aneurysm wall, the radially extending frame portion can be positioned at the aneurysm neck, extend outside of the aneurysm sac, and provide a force to a blood vessel wall near the aneurysm neck, and the blood flow diverter can inhibit flow into the aneurysm.

The blood flow diverter can be implantable in an aneurysm adjacent bifurcated blood vessel branches such that the radially extending frame portion is confined to the bifurcated blood vessel branches. The blood flow diverter can maintain an implanted position without having anchor members positioned in a stem blood vessel. When implanted in an aneurysm adjacent bifurcated blood vessel branches, the expandable shell can inhibit blood flow from the stem blood vessel into the aneurysm sac and divert blood flow into the adjacent bifurcated blood vessel branches.

The combination of the distally extending frame portion and the radially extending frame portion can be sufficient to secure the blood flow diverter at a treatment site.

The blood flow diverter can include a junction joining the distally extending frame portion to the radially extending frame portion, and when the blood flow diverter is implanted, the junction can be positioned centrally within the aneurysm neck.

An example method for treating an aneurysm can include providing a flow diverter having an interior stabilizing frame, an exterior stabilizing frame, and an occluding element, joining the interior stabilizing frame to the exterior stabilizing frame, attaching the occluding element to the interior stabilizing frame, delivering the flow diverter to an aneurysm treatment site, inserting the interior stabilizing frame and the occluding element into an aneurysm sac, expanding the interior stabilizing frame to engage an aneurysm wall from within the aneurysm sac, expanding the occluding element to obstruct at least a portion of an aneurysm neck, expanding the exterior stabilizing frame to engage a blood vessel wall, and blocking the aneurysm neck with the flow diverter to divert a blood flow from the aneurysm to a blood vessel adjacent the aneurysm.

The step of expanding the exterior stabilizing frame can include extending the exterior stabilizing frame through a blood vessel such that the exterior stabilizing frame extends from a first blood vessel branch across the aneurysm neck to a second blood vessel branch opposite the first blood vessel branch, engaging the exterior stabilizing frame to a wall of the first blood vessel branch near the aneurysm neck, and engaging the exterior stabilizing frame to a wall of the second blood vessel branch near the aneurysm neck.

The method can include inducing venous stasis in the aneurysm.

The method can include implanting the flow diverter an aneurysm positioned between branch vessels at a bifurcation and opposite a stem blood vessel and diverting a blood flow from the stem blood vessel to the branch vessels.

The method can include joining the interior stabilizing frame to the exterior stabilizing frame at a frame junction and positioning the frame junction centrally within the aneurysm neck.

The method can include providing an aneurysm treatment with only a single implantation step.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 6A through 6E are cut-away illustrations of implantation steps for implanting an exemplary aneurysm treatment device such as a device illustrated in FIG. 4A, 4B, or 5 according to the present invention;

FIGS. 7 to 10 are flow diagrams each illustrating potential method steps according to the present invention.

DETAILED DESCRIPTION

Figure 1A:
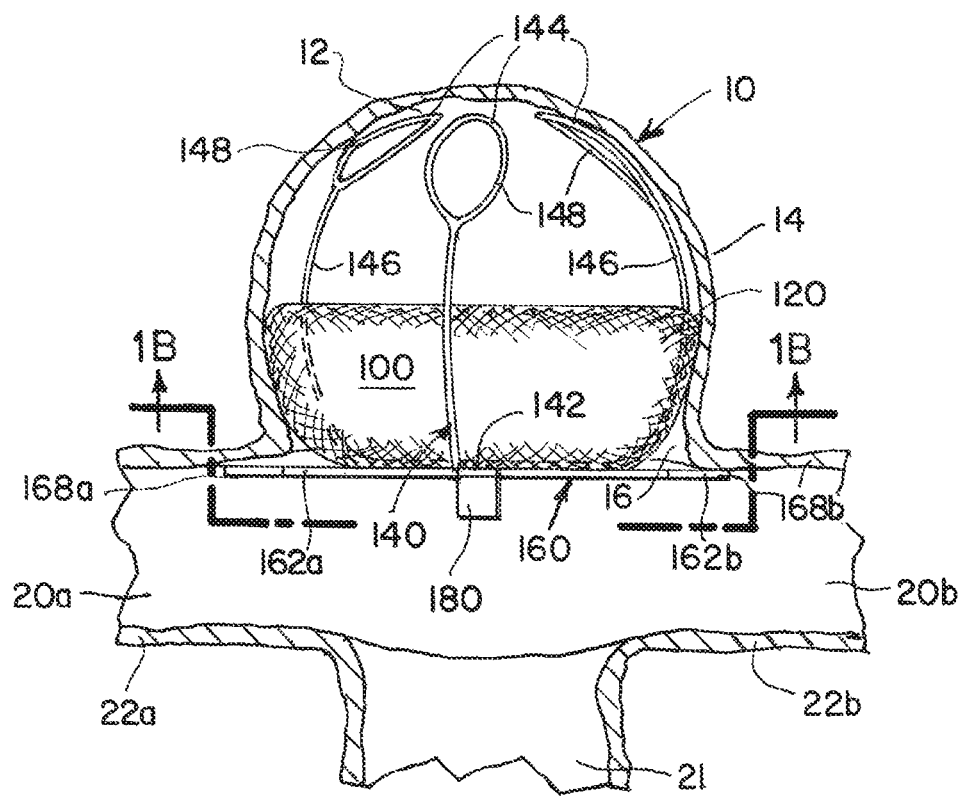
FIG. 1A is a cut-away illustration of an implanted exemplary aneurysm treatment device according to the present invention.

Flow diverters are endovasculature devices that direct blood flow away from an aneurysm. Most flow diverters treat side-wall aneurysms; however, most aneurysms occur at bifurcations. Example aneurysm treatment devices disclosed herein can include flow diverters implantable at a bifurcation and capable of anchoring in place with minimal intrusion into vasculature.

Example devices herein can generally have two parts: 1) a bowl/semi-spherical or spherical shaped occluding portion that nests inside the aneurysm and obstructs the aneurysm neck, directing blood flow away from the aneurysm; and 2) a frame portion that facilitates delivery of the device to a treatment site and stabilizes the occluding portion. The two parts can be attached together at a junction or node. The occluding portion can be made from braided nitinol wire or from nitinol film or sheet. The frame portion can be made from a Nitinol or other memory shape sheet that is laser cut and shape set. The occluding portion, if braided, can be connected to the frame portion by feeding wires of the braid through a hole in the frame portion and then crimping the braid wires. If the occluding portion is a film, it can be connected to the frame portion with a rivet or other means. In the implanted position, the occluding portion and part of the frame portion can reside within the aneurysm sac, extending to the aneurysm wall, and another part of the frame portion can extend below the neck of the aneurysm and engage interior walls of the vasculature to counterbalance the portion of the device within the aneurysm sac. If the occluding portion is bowl shaped, the frame portion can extend distally from a ridge of the bowl and stabilize against the top, distal surfaces of the aneurysm wall.

Turning to the figures, as illustrated in FIGS. 1A through 6F, example aneurysm treatment devices 100 can have an occluding element 120, an interior stabilizing frame 140, an exterior stabilizing frame 160, and an attachment mechanism 180. Devices can be collapsed for delivery to an aneurysm treatment site through a catheter 600 and expanded so that the interior stabilizing frame 140 anchors the occluding element 120 within the aneurysm sac 12, the occluding element 120 extends across the aneurysm neck 16 to inhibit blood flow into the aneurysm sac 12, the exterior frame 160 stabilizes the device 100 by anchoring to vasculature near the aneurysm 10 outside of the sac 12, and the attachment mechanism 180 joins the interior stabilizing frame 140 to the exterior stabilizing frame 160.

Figure 1B:
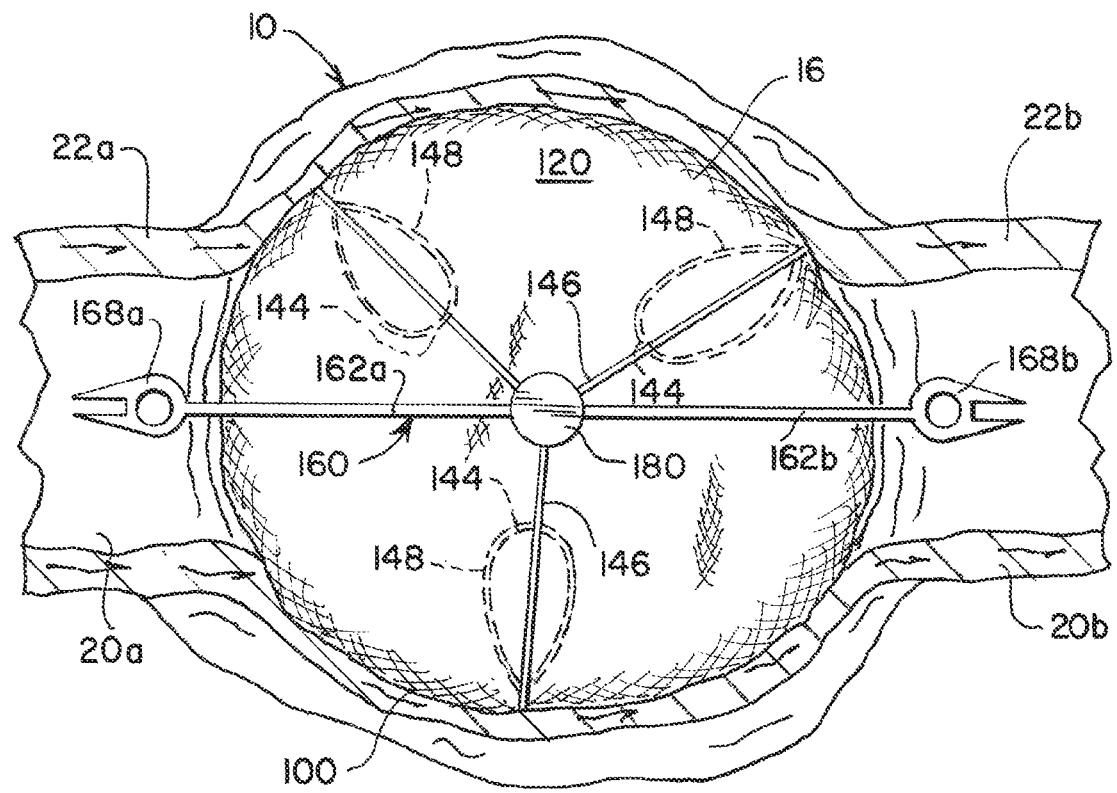
FIG. 1B is a cut-away illustration of the implanted exemplary aneurysm treatment device of FIG. 1A viewed from the proximal end as indicated in FIG. 1A according to the present invention.
Figure 2:
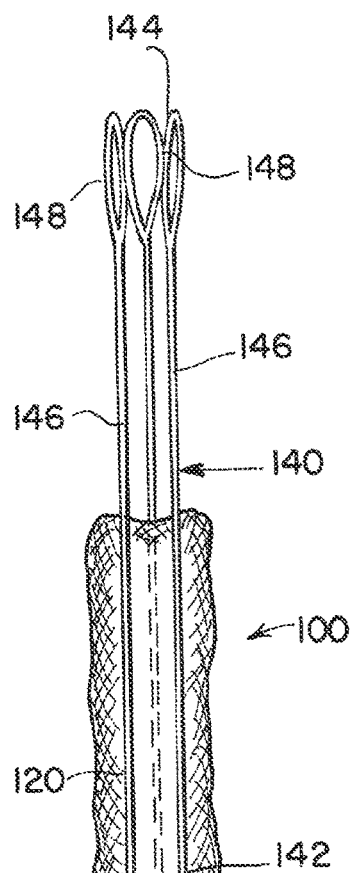
FIG. 2 is an illustration of a collapsed exemplary aneurysm treatment device similar to as shown in FIGS. 1A and 1B according to the present invention.
Figure 3A:
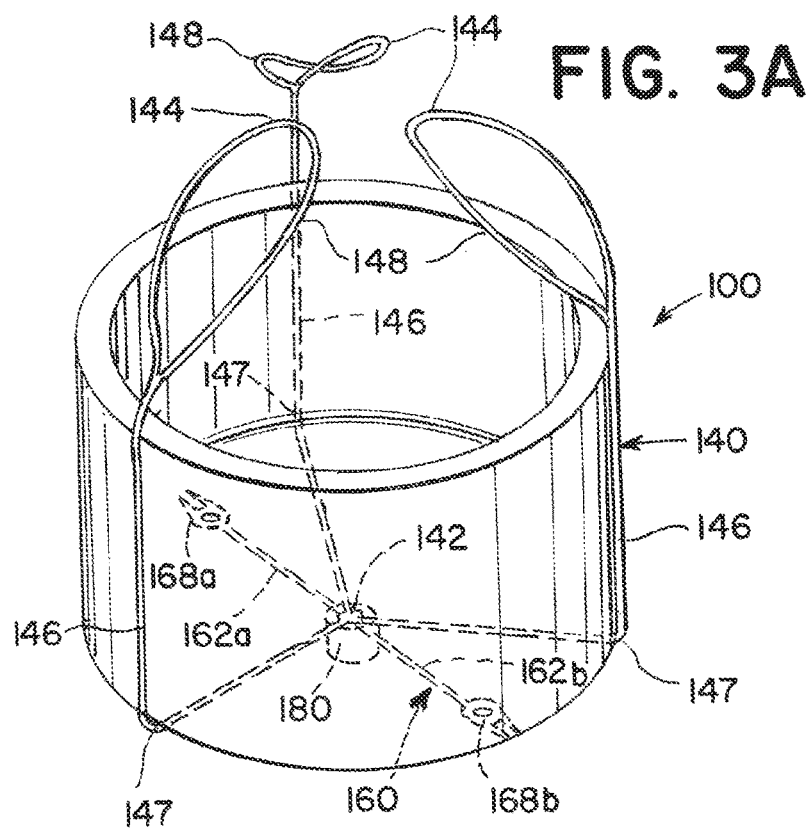
FIGS. 3A and 3B are perspective view illustrations of an exemplary aneurysm treatment device similar to as shown in FIG. 1A, 1B, or 2 in a predetermined shape according to the present invention.
Figure 3B:
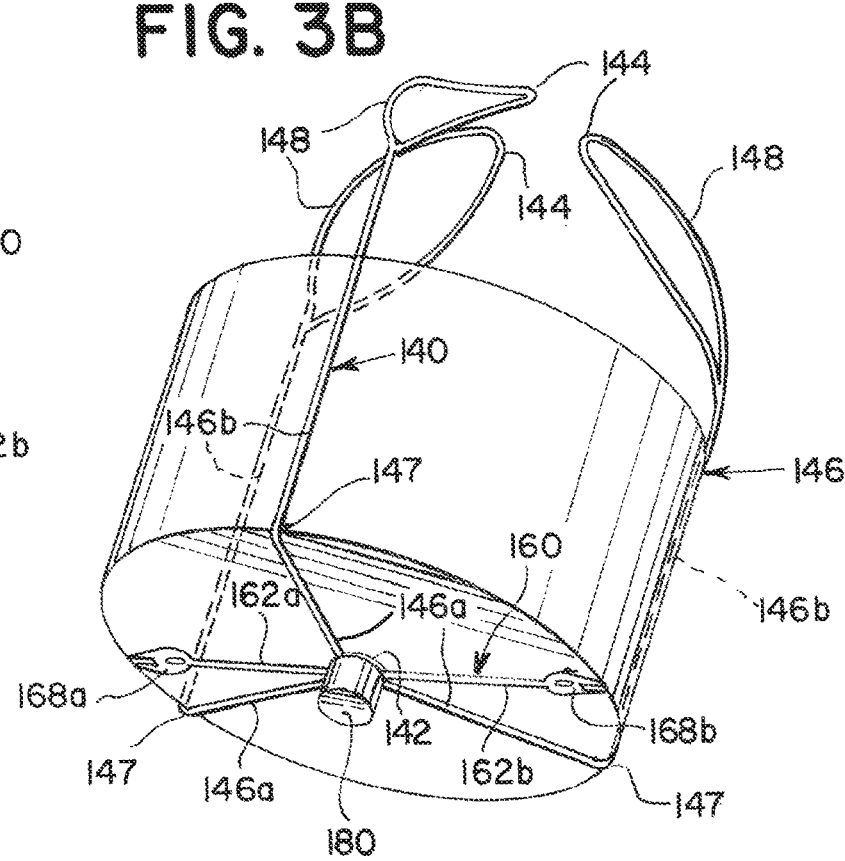

FIGS. 1A through 3B illustrate similarly constructed example devices having a bowl-shaped occlusion device 120, an interior stabilizing frame 140 having multiple elongated members 146 each having a stabilizing segment 148 positioned near its distal end 144, an exterior stabilizing frame 160 having two stabilizing arms 162a,162b, and an attachment mechanism 180 positioned at a central node/frame junction 142 that attaches the interior stabilizing frame 140 to the exterior stabilizing frame 160. FIGS. 1A and 1B illustrate an example device 100 in an implanted position, FIG. 2 illustrates an example device 100 in a collapsed configuration for delivery through a catheter, and FIGS. 3A and 3B illustrate an example device 100 in a predetermined shape.

Referring to FIGS. 1A and 1B, when implanted, the central node 142 can be positioned near the center of the aneurysm neck 16. Each elongated member 146 of the interior stabilizing frame 140 can extend radially from the central node 142 and turn to extend distally into the aneurysm sac 12. The elongated members 146 can each conform to the aneurysm wall 14, thereby anchoring within the aneurysm 10. Stabilizing segments 148 of the elongated members 146 can engage a distal surface of the aneurysm wall 14 to further stabilize the anchoring of the elongated members 146 within the aneurysm 10. Each stabilizing arm 162a,162b of the exterior stabilizing frame 160 can extend radially from the central node 142 to engage a first blood vessel wall 22a in a first blood vessel branch 20a and a second blood vessel wall 22b in a second blood vessel branch 20b. Each stabilizing arm 162a,162b can have a vessel gripper 168a,168b for engaging a blood vessel wall 22a,22b. Bifurcated vessels 20a,20b typically extend opposite each other from a stem blood vessel 21 as illustrated in FIGS. 1A and 1B. Therefore, it is advantageous for each stabilizing arm 162a,162b to be positioned opposite the other to engage walls 22a,22b of blood vessel branches 20a,20b that are positioned opposite each other. Other anatomical geometries exist wherein blood vessel branches are not opposite, and it is contemplated that stabilizing arms could be positioned at an angle with each other in an alternative design (not shown) to better engage blood vessel branches that are not opposite each other.

FIG. 2 is an illustration of an exemplary aneurysm treatment device 100 such as shown in FIGS. 1A and 1B in a collapsed or delivery configuration, sized for delivery through a catheter to a treatment site. In the delivery configuration, elongated members 146 can extend distally and stabilizing arms 162a,162b can extend proximally such that stabilizing segments 148 of the interior stabilizing frame 140 are positioned at a distal end 144 of the device 100 and vessel grippers 168a,168b are positioned at a proximal end of the device 100. As illustrated, the occluding element 120 can be a braided mesh that is collapsed within the interior stabilizing frame 140. Alternatively, the occluding element can be a film. The attachment mechanism 180 can serve as an attachment point for manipulating the device 100 during delivery through the microcatheter and implantation in the aneurysm 10.

FIGS. 3A and 3B are perspective view illustrations of an exemplary aneurysm treatment device such as shown in FIG. 1A, 1B, or 2 in a predetermined shape. All or portions of the device 100 can be made from a memory shape material or materials having a first, predetermined shape and a second, deformed shape. The memory shape materials can be in the second, deformed shape when the device is in the collapsed configuration and can move to a third, deployed shape when the device in the implanted or deployed configuration. The third, deployed shape can be based at least in part on the predetermined shape and the shape of the aneurysm wall.

An example device 100 can have a first, predetermined shape as shown in FIGS. 3A and 3B, a second, deformed shape as shown in FIG. 2, and a third, deployed shape as illustrated in FIGS. 1A and 1B. Memory shape materials of which the device 100 can be made include Nitinol, Nitinol alloys, polymer memory shape material, or other memory shape material having properties for reshaping as described herein. The device 100 can be in a deformed shape in the collapsed configuration and can reshape based on a predetermined shape after exiting the microcatheter. Example devices described herein can be collapsed to the deformed shape for delivery through a catheter to a treatment site and can expand toward the predetermined shape in response to a change in temperature due to contacting blood or bodily fluid after exiting a catheter.

Referring to FIGS. 3A and 3B, the interior stabilizing frame 140 can be made of memory shape material and can have a predetermined shape. In the predetermined shape each elongated member 146 can have a first segment 146a that extends primarily in a radial direction from the central node 142 toward a bend 147 of about 90° and a second segment 146b extending from the bend 147 primarily in a distal direction. Such a shape can be advantageous for wide-necked aneurysms to achieve maximum extension across the aneurysm neck during implantation as each first segment 146a can be sized longer than the radius of the aneurysm neck 16 so that each first segment 146a extends to engage the aneurysm wall 14 approximate each bend 147 when the device 100 is implanted. In the predetermined shape each stabilizing segment 148 can curve inwardly and have an atraumatic shape. Such a shape can be advantageous for stabilizing the interior stabilizing frame 140 within the aneurysm sac 12 by engaging a distal surface of the aneurysm wall 14 without providing excessive force against the distal surface that could cause the aneurysm to rupture.

The occluding element 120 can have a predetermined shape that is substantially cylindrical, and bowl shaped as illustrated in FIGS. 3A and 3B. For some treatments it can be advantageous for the occluding element 120 to have a diameter of about 8 mm and a height of about 5 mm.

Figure 4B:
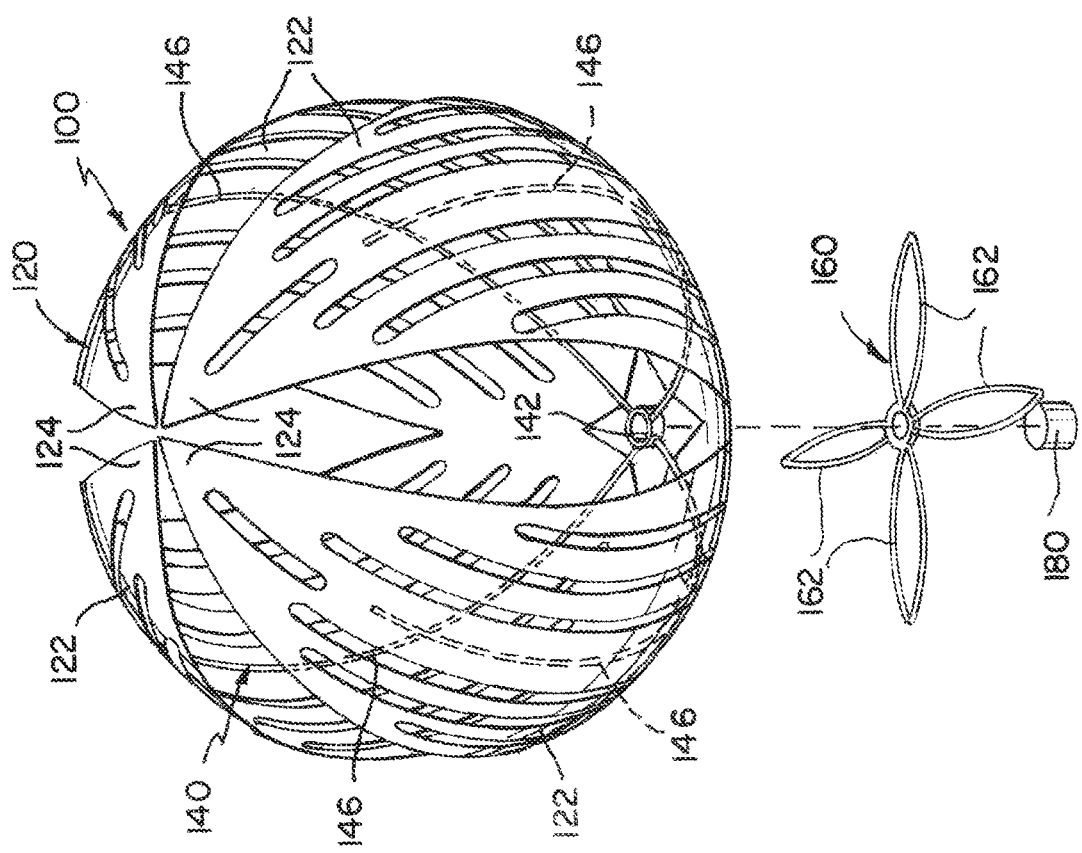
FIG. 4B is an exploded perspective view illustration of an exemplary aneurysm treatment device in a predetermined shape similar to as shown in FIG. 4A according to the present invention.
Figure 4A:
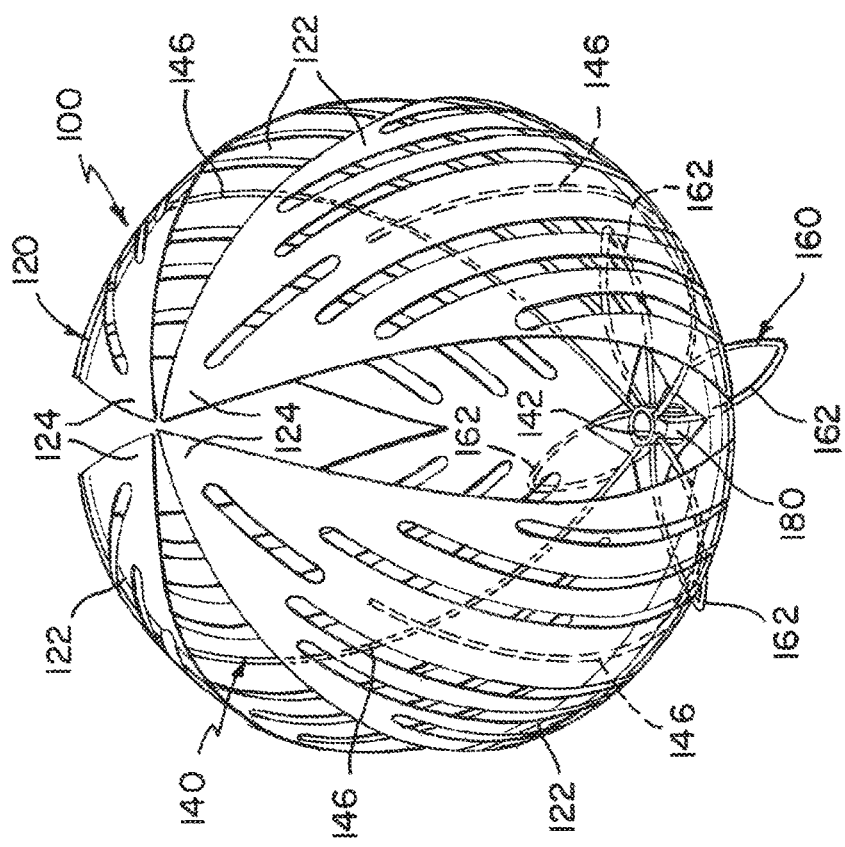
FIG. 4A is a perspective view illustration of an exemplary aneurysm treatment device in a predetermined shape according to the present invention.
Figure 5:
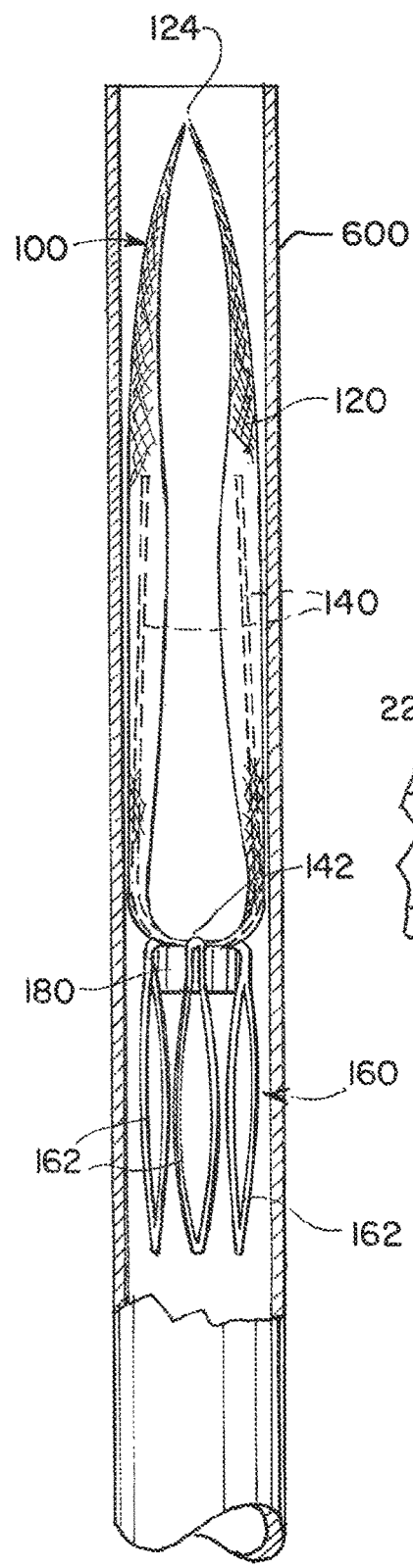
FIG. 5 is a cut-away illustration of an exemplary aneurysm treatment device in a collapsed or delivery configuration within a catheter, the exemplary aneurysm treatment device similar to that illustrated in FIG. 4A or 4B according to the present invention.

FIGS. 4A through 6F illustrate similarly constructed example devices 100 having a spherically shaped occluding element 120, an interior stabilizing frame 140 having multiple elongated members 146, an exterior stabilizing frame 160 having multiple stabilizing extensions 162, and an attachment mechanism 180 positioned at a central node/frame junction 142. FIG. 4A illustrates a perspective view of a device 100 in a predetermined shape. FIG. 4B illustrates the device 100 of FIG. 4A in a perspective exploded view, FIG. 5 illustrates an example device 100 in a collapsed configuration for delivery through a catheter, and FIGS. 6A through 6F illustrate an example device 100 in stages of implantation. Each device illustrated in FIGS. 4A through 6F is depicted with an occluding element 120 having four leaf shaped films 122 attached to the interior stabilizing frame 140 and extending from near the central node 142 to a distal end 124 of each leaf 122.

Referring to FIGS. 4A and 4B, when the device 100 is in a predetermined shape, the combination of the interior stabilizing frame 140 and the occluding element 120 can form a substantially spherical shape. As aneurysms can commonly have an approximately spherically shaped interior wall 14, the spherical predetermined shape can be advantageous for providing a large surface area for contacting a majority of the surface of the interior wall 14 of the aneurysm 10, thereby providing a large area over which to engage and anchor. A spherical predetermined shape can also provide a larger area over which the interior stabilizing frame 140 and occluding element 120 press against the wall 14 of the aneurysm 10, thereby distributing force applied to the aneurysm wall 14 by the device 100 and minimizing any localized high force pressure points to reduce the chance of aneurysm rupture due to the treatment.

The occluding element 120 can be laser cut from a single sheet of material as one piece, or each leaf 122 can be cut individually as separable pieces. Leaves 122 can be attached to each other or overlap within the region of the device 100 that would be placed across the aneurysm neck 16 when implanted, i.e. regions near the central node 142. As illustrated, leaves 122 can include cutouts to reduce the total volume of the device 100 and facilitate the occluding element 120 collapsing to a smaller diameter for easier delivery through a catheter to a treatment site. Leaves 122 can be attached to each other at each distal end 124.

Continuing with FIGS. 4A and 4B, the exterior stabilizing frame 160 can have multiple stabilizing arms or extensions 162, and the stabilizing arms/extensions 162 can have a leaf or marquis shape. A design incorporating multiple extensions 162 can potentially be implanted in multiple rotational orientations, and in some instances, can be implanted in an orientation that is independent of the alignment of the vasculature adjacent the aneurysm neck. Each extension 162 can have an atraumatic end.

FIG. 5 is an illustration of an exemplary aneurysm treatment device 100 such as shown in FIGS. 4A and 4B in a collapsed or delivery configuration, sized for delivery through a catheter 600 to a treatment site. In the delivery configuration, the interior stabilizing frame 140 can extend distally from the central node 142 and the exterior stabilizing frame 160 can extend proximally from the central node 142. The occluding element 120 can be attached to the interior stabilizing frame 140 and extend distally from the central node 142. The distal ends 124 of each leaf 122 of the occluding element 120 can define a distal end of the device.

FIGS. 6A through 6E are cut-away illustrations of implantation steps for implanting an exemplary aneurysm treatment device 100 such as a device illustrated in FIG. 4A, 4B, or 5. As shown, the device 100 can be implanted in an aneurysm 10 positioned at a bifurcation and the catheter 600 can reach the treatment site through a stem blood vessel 21. Although not shown, the device 100 can be implanted in an aneurysm positioned on a vessel sidewall, and a catheter can reach a treatment site through the vessel as would be understood by a person of ordinary skill in the art.

Figure 6A:
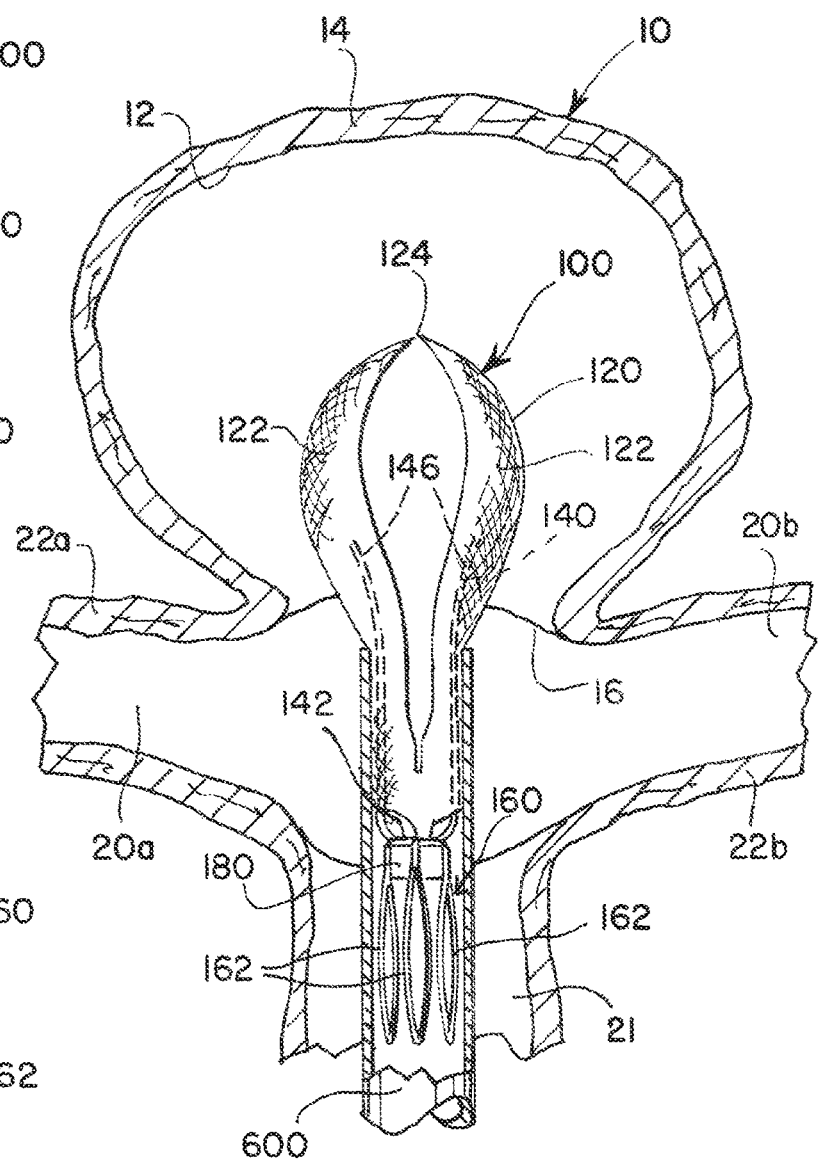

FIG. 6A is a cut-away illustration of the device 100 exiting the catheter 600 and expanding as it traverses through the aneurysm neck 16 and into the sac 12 of the aneurysm 10. The interior stabilizing frame 140 can have a predetermined shape, and as the interior stabilizing frame 140 exits the catheter 600, the interior stabilizing frame 140 can expand toward the predetermined shape. The interior stabilizing frame 140 can be made from a memory shape material, and the predetermined shape can be made by heat setting the interior stabilizing frame 140 prior to implanting the device 100. The occluding element 120 can also expand toward a predetermined shape as it exits the catheter 600 and can also be made from a memory shape material that is heat set prior to implanting the device 100. The interior stabilizing frame 140 and occluding element 120 can move toward the predetermined shape in response to a temperature change due to contact with blood or bodily fluid.

Figure 6C:
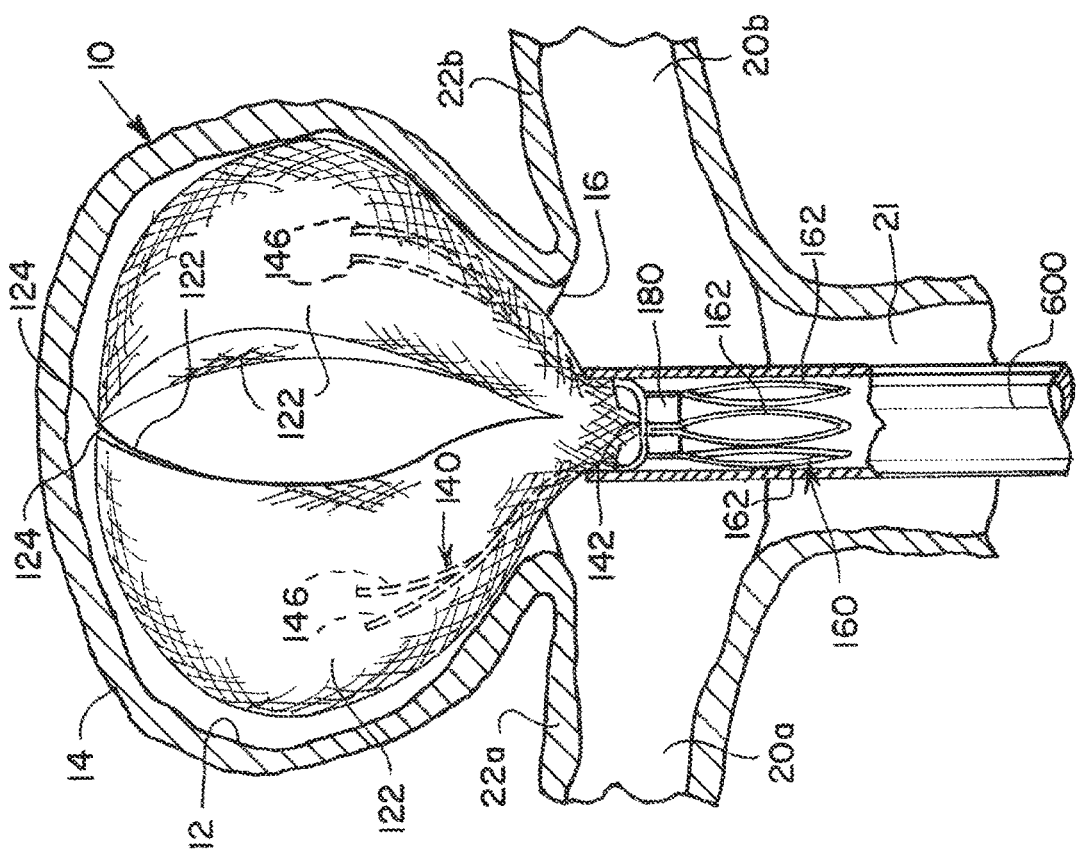
Figure 6B:
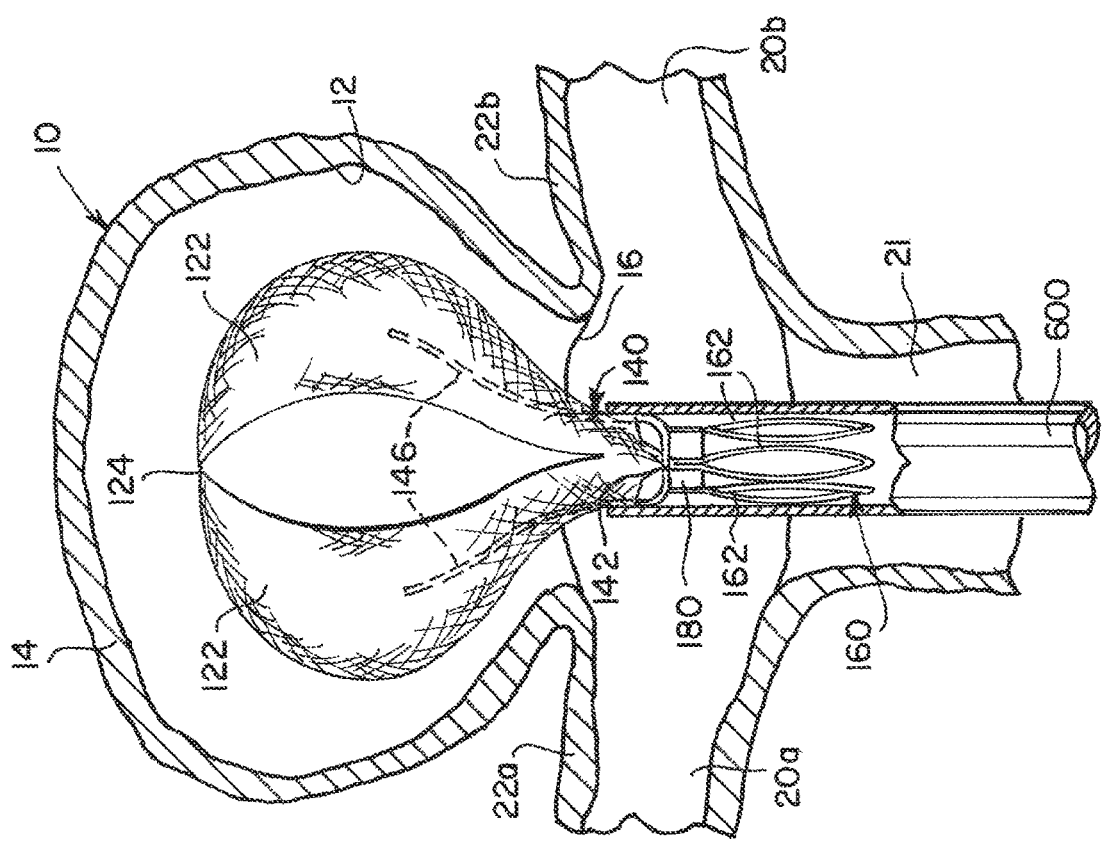

FIG. 6B illustrates the occluding element 120 and the interior stabilizing frame 140 continuing to expand as they exit the catheter 600.

FIG. 6C illustrates the occluding element 120 and the interior stabilizing frame 140 extending to contact the aneurysm wall 14 as they are nearly fully expelled from the catheter 600.

FIG. 6D illustrates the expansion of the exterior stabilizing frame 160 as the catheter 600 is pulled proximally to expose the exterior stabilizing frame 160. The exterior stabilizing frame 160 can be made of a memory shape material, and the predetermined shape can be made by heat setting the exterior stabilizing frame 160 prior to implanting the device 100. The exterior stabilizing frame 160 can move toward the predetermined shape as the catheter 600 is pulled proximally to expose the exterior stabilizing frame 160. The exterior stabilizing frame 160 can move toward the predetermined shape in response to a temperature change due to contact with blood or bodily fluid. In FIG. 6D, the occluding element 120 and interior stabilizing frame 140 are shown fully extended to an implanted configuration, engaging the aneurysm wall 14.

FIG. 6E illustrates the exterior stabilizing frame 160 in a final, implanted position, thereby completing implantation of the device 100. Stabilizing extensions 162 of the exterior stabilizing frame 160 can extend across the aneurysm neck 16 and engage surfaces of vascular walls 22a,22b adjacent to the neck 16 of the aneurysm 10. Once the device 100 is implanted, the catheter 600 can be extracted or repositioned as needed for the treatment.

Figure 6F:
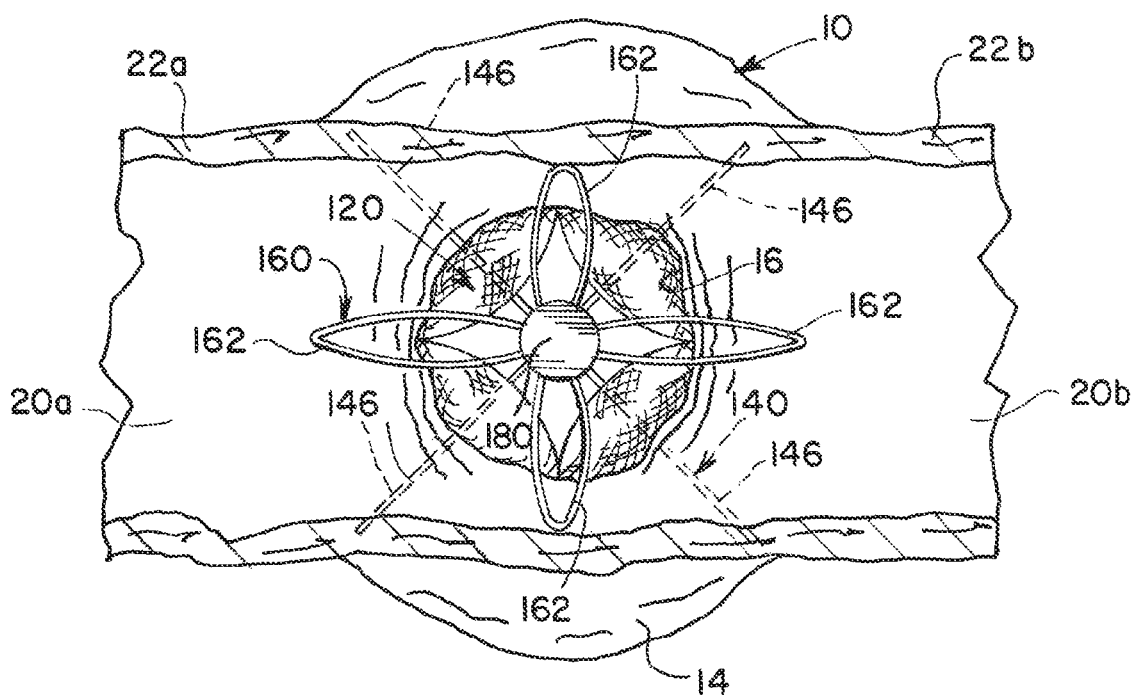
FIG. 6F is a cut-away illustration of the implanted exemplary aneurysm treatment device of FIG. 6E viewed from the proximal end of the device as indicated in FIG. 6E according to the present invention.

FIG. 6F is a cut-away illustration of the implanted exemplary aneurysm treatment device 100 of FIG. 6E viewed from the proximal end of the device as indicated in FIG. 6E. As illustrated, the exterior stabilizing frame 160 of the device 100 can have four stabilizing extensions or arms 162. As shown, the four stabilizing extensions 162 can be aligned such that two extensions 162 extend into branch vessels 20a,20b and the other two extensions 162 extend orthogonal to the branch vessels 20a,20b. Positioned thusly, the extensions 162 extending into the branch vessels 20a,20b can be substantially straight when implanted, and the orthogonal extensions 162 can be curved when implanted to follow the curvature of the anatomy of the vasculature. It is contemplated that the exterior stabilizing frame 162 having four extensions 162 that can be oriented at various rotational alignments in relation to the branch vessels 20a,20b, and it is not necessary for any of the extensions 162 to align with the branch vessels 20a,20b in order to effectively stabilize the device 100. For example, each extension 162 can be oriented at about 45° in relation to a branch vessel 20a,20b such that each extension 162 both extends into one of the branch vessels 20a,20b and curves to follow a curvature of the circumference of the respective branch vessel 20a,20b.

It is contemplated that the exterior stabilizing frame 162 can be effective at stabilizing the device 100 when implanted at any rotational orientation relative to the branch vessels 20a,20b. Having the option for multiple or infinite rotational alignments can make the device 100 easier to position during implantation.

Although not shown, it is to be understood that example devices illustrated in FIGS. 1A through 3B can be implanted according to the principles and steps illustrated in FIGS. 6A through 6E.

It is to be understood that a device 100 can be constructed and used by mixing and matching elements from the various examples. For example, an interior stabilizing frame 140 constructed as illustrated in FIGS. 1A through 3B can be used in combination with an exterior stabilizing frame 160 constructed as illustrated in FIGS. 4 through 6F, an interior stabilizing frame 140 constructed as illustrated in FIGS. 4 through 6F can be used in combination with an exterior stabilizing frame 160 constructed as illustrated in FIGS. 1A through 3B, an interior stabilizing frame 140 constructed as illustrated in FIGS. 1A through 2 can have a spherical predetermined shape similar to as illustrated in FIGS. 4A and 4B, the occluding element 120 can be constructed of braided mesh or from a laser cut sheet in any of the examples illustrated in FIGS. 1A through 6F, and the exterior stabilizing frame 160 can include a number of stabilizing arms or elements 162 shaped as illustrated in any of the examples illustrated in FIGS. 1A through 6F or shaped as would otherwise be understood by a person of ordinary skill in the art.

FIGS. 7 through 10 are flow diagrams outlining example method steps for treating an aneurysm. The method steps can be implemented by any of the example means described herein or by any means that would be known to a person of ordinary skill in the art.

Referring to a method 700 outlined in FIG. 7, in step 710 a flow diverter having an interior stabilizing frame, an exterior stabilizing frame, and an occluding element can be provided. In step 720, the interior stabilizing frame can be joined to the exterior stabilizing frame. In step 730, the occluding element can be attached to the interior stabilizing frame. In step 740, the flow diverter can be delivered to an aneurysm treatment site. In step 750, the interior stabilizing frame and the occluding element can be inserted into an aneurysm sac. In step 760, the interior stabilizing frame can be expanded to engage an aneurysm wall from within the aneurysm sac. In step 770, the occluding element can be expanded to obstruct at least a portion of an aneurysm neck. In step 780, the exterior stabilizing frame can be expanded to engage a blood vessel wall. In step 790, the aneurysm neck can be blocked with the flow diverter to divert a blood flow from the aneurysm to a blood vessel adjacent to the aneurysm.

Figure 8:
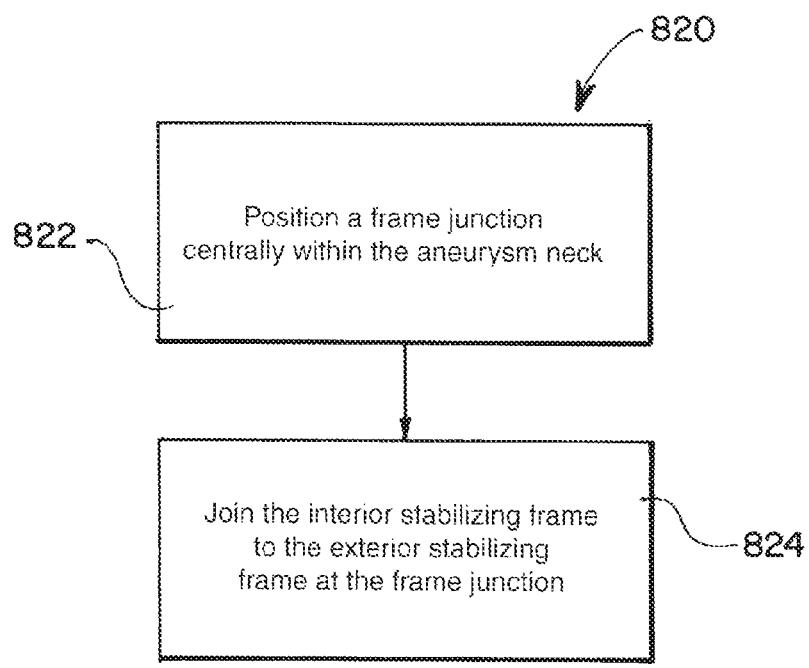

The method 700 illustrated in FIG. 7 can further include one or more of the method steps illustrated in FIG. 8. Referring to the method steps 820 illustrated in FIG. 8, in step 822 a frame junction can be positioned centrally within the aneurysm neck. In step 824, the interior stabilizing frame can be joined to the exterior stabilizing frame at the frame junction.

Method step 780 illustrated in FIG. 7, expanding the exterior stabilizing frame to engage the blood vessel wall can include one or more steps of a sub-method 880 illustrated in FIG. 9. Referring to the sub-method 880 illustrated in FIG. 9, in step 882 the exterior stabilizing frame can be extended through the blood vessel from a first blood vessel branch across the aneurysm neck to a second blood vessel branch. In step 884, the exterior stabilizing frame can engage the first blood vessel wall approximate the aneurysm neck in the first blood vessel branch. In step 886 the exterior stabilizing frame can engage to a second blood vessel wall approximate the aneurysm neck in the second blood vessel branch positioned opposite the first blood vessel branch.

The method 700 illustrated in FIG. 7 can further include one or more of the method steps illustrated in FIG. 10. Referring to the method steps 890 illustrated in FIG. 10, in step 892 the flow diverter can be implanted in the aneurysm, wherein the aneurysm is positioned between bifurcated blood vessels and positioned opposite a stem blood vessel. In step 894, the blood flow can be diverted from the stem blood vessel to the bifurcated vessels. In step 896, venous stasis can be induced in the aneurysm. In step 898, an aneurysm treatment can be provided with only a single implantation step.

The descriptions contained herein are examples of embodiments of the invention and are not intended in any way to limit the scope of the invention. As described herein, the invention contemplates many variations and modifications of the device including using alternative geometries of structural elements, combining shapes and structural elements from various example embodiments, using alternative materials, etc. It is also contemplated that devices can be used to treat sidewall aneurysms, and examples are not intended to limit the application of the device to aneurysms that are positioned at a bifurcation or to treatment of wide necked aneurysms. These modifications would be apparent to those having ordinary skill in the art to which this invention relates and are intended to be within the scope of the claims which follow.

The invention claimed is:

1. A device for treating an aneurysm comprising:
a central node positioned approximate a center of an aneurysm neck;
an interior stabilizing frame extending radially from the central node comprising three or more elongated members and configured to extend distally into an aneurysm sac and engage an aneurysm wall, each of the three or more elongated members comprising:
a first end positioned approximate the central node;
a first segment configured to extend radially from the first end across at least a portion of the aneurysm neck;
a second segment configured to extend distally and conform to the aneurysm wall; and
a stabilizing segment positioned on a distal end of the second segment, the stabilizing segment comprising an inwardly curved closed loop configured to engage a distal surface of the aneurysm wall;
the first segment adjoining the second segment at an angle measuring approximately 90 degrees;
an exterior stabilizing frame affixed to the interior stabilizing frame at the central node, extending radially from the central node and configured to engage a first blood vessel wall in a first blood vessel branch and engage a second blood vessel wall in a second blood vessel branch; and
an occluding element affixed to the interior stabilizing frame configured to be at least partially disposed in the aneurysm sac and extend across at least a portion of the aneurysm neck and obstruct a majority of the aneurysm neck.

2. The device of claim 1 wherein the combination of the interior stabilizing frame and the exterior stabilizing frame is sufficient to maintain the position of the device at an aneurysm treatment site.

3. The device of claim 1 wherein the sole combination of the interior stabilizing frame and the exterior stabilizing frame affixes the device to an aneurysm treatment site.

4. The device of claim 1 wherein the occluding element self-expands to conform to the aneurysm wall.

5. The device of claim 1 wherein the occluding element completely obstructs the aneurysm neck.

6. The device of claim 1 wherein the occluding element is configured to at least partially fill the aneurysm sac.

7. The device of claim 1 wherein the exterior stabilizing frame comprises:
 a first stabilizing arm extending in a first direction from the central node configured to engage the first blood vessel wall approximate the aneurysm neck; and
 a second stabilizing arm extending in a second direction opposite the first direction from the central node configured to engage the second blood vessel wall approximate the aneurysm neck.

8. The device of claim 1 wherein the occluding element comprises a plurality of oblong leaf structures each configured to extend from the aneurysm neck radially and distally, at least partially conform to the aneurysm wall, and converge at a distal end positioned at a distal surface of the aneurysm wall.

9. A blood flow diverter for treating an aneurysm comprising:
 a central node positioned approximate a center of an aneurysm neck;
 a distally extending frame portion configured to be positioned within an aneurysm sac and provide a force against an aneurysm wall from within the aneurysm sac, the distally extending frame portion comprising a stabilizing segment positioned on a distal end of the distally extending frame portion, the stabilizing segment comprising an inwardly curved closed loop configured to engage a distal surface of the aneurysm wall;
 an expandable shell joined to the distally extending frame portion, the expandable shell configured to extend across at least a portion of the aneurysm neck and conform to the aneurysm wall such that at least a portion of the distally extending frame is configured to be positioned between the expandable shell and the aneurysm wall; and
 a radially extending frame portion attached to the distally extending frame portion at the central node configured to be positioned at the aneurysm neck, extend outside of the aneurysm sac, and provide a force to a blood vessel wall approximate the aneurysm neck, and wherein the blood flow diverter is configured to inhibit a blood flow into the aneurysm.

10. The blood flow diverter of claim 9 implantable in an aneurysm adjacent bifurcated blood vessel branches wherein the radially extending frame portion is confined to the bifurcated blood vessel branches.

11. The blood flow diverter of claim 9 implantable in an aneurysm adjacent bifurcated blood vessel branches wherein the expandable shell inhibits a blood flow from a stem blood vessel into the aneurysm sac and diverts the blood flow into bifurcated blood vessel branches.

12. The blood flow diverter of claim 9 wherein the combination of the distally extending frame portion and the radially extending frame portion are sufficient to secure the blood flow diverter at a treatment site.

13. The blood flow diverter of claim 9 further comprising a junction configured to be positioned centrally within the aneurysm neck and join the distally extending frame portion to the radially extending frame portion.

14. A method for treating an aneurysm comprising the steps of:
 providing a flow diverter comprising an interior stabilizing frame, an exterior stabilizing frame, and an occluding element, wherein the interior stabilizing frame comprises three or more elongated members each comprising:
 a first end positioned approximate a central node;
 a first segment configured to extend radially from the first end across at least a portion of an aneurysm neck;
 a second segment configured to extend distally and conform to an aneurysm wall; and
 a stabilizing segment positioned on a distal end of the second segment, the stabilizing segment comprising an inwardly curved closed loop configured to engage a distal surface of the aneurysm wall;
 the first segment adjoining the second segment at an angle measuring approximately 90 degrees;
 joining the interior stabilizing frame to the exterior stabilizing frame at the central node positioned approximate a center of the aneurysm neck;
 attaching the occluding element to the interior stabilizing frame;
 delivering the flow diverter to an aneurysm treatment site;
 inserting the interior stabilizing frame and the occluding element into an aneurysm sac;
 expanding the interior stabilizing frame to engage the aneurysm wall from within the aneurysm sac;
 expanding the occluding element to obstruct at least a portion of the aneurysm neck;
 expanding the exterior stabilizing frame to engage a blood vessel wall; and
 blocking the aneurysm neck with the flow diverter to divert a blood flow from the aneurysm to a blood vessel adjacent the aneurysm.

15. The method of claim 14 wherein the step of expanding the exterior stabilizing frame further comprises the steps of:
 extending the exterior stabilizing frame through a blood vessel from a first blood vessel branch, across the aneurysm neck, to a second blood vessel branch;
 engaging the exterior stabilizing frame to a first blood vessel wall approximate the aneurysm neck in the first blood vessel branch; and
 engaging the exterior stabilizing frame to a second blood vessel wall approximate the aneurysm neck in the second blood vessel branch positioned opposite the first blood vessel branch.

16. The method of claim 14 further comprising the step inducing venous stasis in the aneurysm.

17. The method of claim 14 further comprising the steps of:
 implanting the flow diverter in an aneurysm, the aneurysm positioned between bifurcated blood vessels opposite a stem blood vessel; and
 diverting a blood flow from the stem blood vessel to the bifurcated vessels.

18. The method of claim 14 further comprising the steps of:
 positioning a frame junction centrally within the aneurysm neck; and joining the interior stabilizing frame to the exterior stabilizing frame at the frame junction.

* * * * *